United States Patent [19]
Atkinson et al.

[11] Patent Number: 5,402,667
[45] Date of Patent: * Apr. 4, 1995

[54] MONITORING OF SOIL

[75] Inventors: Dick T. Atkinson, Nashua, N.H.; James E. Aplin, Needham, Mass.; Arnis Mangolds, Stow, Mass.; Daniel J. Foley, North Chelmsford, Mass.

[73] Assignee: Gas Research Institute, Chicago, Ill.

[*] Notice: The portion of the term of this patent subsequent to Apr. 21, 2009 has been disclaimed.

[21] Appl. No.: 934,611
[22] PCT Filed: Mar. 7, 1991
[86] PCT No.: PCT/US91/01573
§ 371 Date: Sep. 29, 1992
§ 102(e) Date: Sep. 29, 1992
[87] PCT Pub. No.: WO91/14181
PCT Pub. Date: Sep. 19, 1991

Related U.S. Application Data

[63] Continuation-in-part of Ser. No. 490,751, Mar. 8, 1990, Pat. No. 5,105,650.

[51] Int. Cl.⁶ .................. G01N 29/18; G01N 33/24
[52] U.S. Cl. .................. 73/12.12; 73/594; 73/866
[58] Field of Search .................. 73/866, 12.01, 594, 73/597, 84, 784, 12.08–12.14

[56] References Cited

U.S. PATENT DOCUMENTS

| | | | |
|---|---|---|---|
| Re. 31,195 | 4/1983 | Thurner | 73/573 |
| 2,284,707 | 6/1942 | Wilson . | |
| 2,336,500 | 12/1943 | Osterberg | 177/351 |
| 2,624,251 | 1/1953 | Porter . | |
| 3,286,514 | 11/1966 | Anderson . | |
| 3,372,577 | 3/1968 | Bates et al. . | |
| 3,456,496 | 7/1969 | Heller | 338/2 X |
| 3,492,859 | 2/1970 | Dodge | 73/84 X |
| 3,529,468 | 9/1970 | Carlson . | |
| 3,537,541 | 11/1970 | Desai et al. | 73/597 |
| 3,641,811 | 2/1972 | Gnaedinger, Jr. et al. . | |
| 3,998,090 | 12/1976 | Wislocki | 73/12.13 X |
| 4,149,253 | 4/1979 | Paar et al. | 364/505 |
| 4,348,901 | 9/1982 | Vural et al. | 73/594 |
| 4,398,427 | 8/1983 | Pan | 73/784 |
| 4,495,434 | 1/1985 | Diepers et al. | 310/338 |
| 4,524,626 | 6/1985 | Pabst et al. | 73/84 X |
| 4,543,820 | 10/1985 | Handy et al. | 73/84 |
| 4,590,802 | 5/1986 | Furmanski | 73/573 |
| 4,614,110 | 9/1986 | Osterberg | 73/84 |
| 4,662,226 | 5/1987 | Wang | 73/728 |
| 4,802,371 | 2/1989 | Calderara et al. | 73/DIG 4 X |
| 4,856,318 | 8/1989 | Hogan et al. | 73/82 X |
| 5,024,090 | 6/1991 | Pettigrew et al. | 73/594 X |
| 5,054,490 | 10/1991 | Rossmon et al. | 73/594 X |
| 5,105,650 | 4/1992 | Atkinson et al. | 73/784 X |
| 5,247,937 | 9/1993 | Ophir et al. | 73/597 X |

FOREIGN PATENT DOCUMENTS

WO89/07176 8/1989 WIPO .

OTHER PUBLICATIONS

Database WPI, Week 8842, Derwent Publications Ltd., London, GB; AN 88-299228 & SU-A-1 388 799 (Ind Build Res Inst) 15 Apr. 1988 (Abstract).
Database WPI, Week 8926, Derwent Publications Ltd., London, GB; AN 89-191447 & SU-A-1 449 864 (Urals Rail Transp Inst) 7 Jan. 1989, (Abstract).

Primary Examiner—Tom Noland
Attorney, Agent, or Firm—Fish & Richardson

[57] ABSTRACT

Methods and apparatus for monitoring the compaction of soil material in a defined region include hammer structure for impacting soil material in the defined region, a sensor for disposition at the bottom of the defined region the includes a transducer for developing an electric signal in response to energy transmitted through soil material from the hammer structure, and a control module responsive to electric signals from the sensor for providing an indication of the quality of compaction of soil material in the defined region.

6 Claims, 5 Drawing Sheets

Fig. 9

MONITORING OF SOIL

This application is a U.S. National Stage application of International Application No. PCT/US91/01573, filed Mar. 7, 1991, which was a continuation-in-part of U.S. application Ser. No. 07/490,751, filed Mar. 8, 1990, and issued Apr. 21, 1992 as U.S. Pat. No. 5,105,650.

BACKGROUND OF THE INVENTION

This invention relates to monitoring systems and more particularly to methods and apparatus for monitoring soil such as compaction of backfill for utility excavations and the like.

Excavations such as utility trenches, foundations and the like are generally backfilled in layers, termed lifts, with each lift of backfill material be compacted prior to the addition of the next lift. If backfill material is improperly compacted, or if an unsuitable backfill material is used, the backfilled excavation may subside. Subsidence in foundations, roadways or other structures due to improper backfill compaction can necessitate costly and disruptive repairs.

In the proper compaction of backfill in an excavation, each backfill lift should be properly compacted prior to the addition of the next lift; and after all lifts are in place and compacted, the complete backfilled excavation should be proofed to verify that there are no voids, soil bridges, or layers that are not fully compacted. Current monitoring methods such as drop hammer penetration probes, nuclear densitometry and the sand cone method are typically used only to check each lift for proper compaction, and such methods are expensive, time-consuming and cannot be performed in real time.

Tests for acceptable compaction of soil material such as Proctor or California Bearing Ratio (CBR) require specialized equipment and significant amounts of time to perform, and accordingly are usually performed in a laboratory rather than in the field.

SUMMARY OF THE INVENTION

In accordance with one aspect of the invention, there is provided apparatus for monitoring the compaction of soil material in a defined region such as a chamber or an excavation that includes hammer structure for delivering impact energy to soil material in the defined region, sensor structure for disposition at the bottom of the defined region that includes a transducer for developing an electric signal in response to energy transmitted through soil material from the hammer structure, and a control module responsive to electric signals from the sensor structure for providing an indication of the quality of compaction of soil material in the defined region.

In a preferred embodiment for providing an indication of the quality of compaction of backfill material in an excavation, the apparatus includes a sensor module with a compliant base member of area at least about one-half the area of the base of the excavation to be backfilled. The base member is of electrically-insulating material such as rubber, synthetic rubber, paper, styrofoam or similar polymeric material on which a plurality of piezoelectric transducers are secured in spaced array, together with an overlying protective sheet member, an array of first piezoelectric transducers disposed along the perimeter of the base member being connected in parallel to a first output conductor and a second piezoelectric transducer generally at the center of the base member being connected to a second output conductor, the output conductors being connected to the control module for transmitting electrical signals to the control module.

Supplemental proofing apparatus includes a hammer and a third piezoelectric transducer for placement on the top of the backfilled excavation. The control module includes accumulator circuitry for accumulating output signals from the sensor array for providing an indication of the quality of compaction of each lift of backfill material in the excavation, and verifying circuitry responsive to the second and third transducers for providing a transit time (dependent on seismic velocity) indication of impact energy propagation between the third transducer at the top of the backfill material and the second transducer at the bottom of the excavation.

In a particular embodiment, the control module includes peak detection circuitry for sampling electrical signals received from the array of first piezoelectric transducers, circuitry for storing indications of the peak amplitude of signals received during a sequence of compaction intervals, circuitry responsive to the storage circuitry for providing average peak value signals during a pass of the hammer structure such as a compacting tool, comparison circuitry for comparing average peak value signals during a previous compaction pass with average peak value signals during the current compaction pass to provide an indication of the progress of the compaction process; and timing circuitry for providing an indication of impact energy propagation time through backfill material to provide an indication of acceptable compaction after the excavation backfill process has been completed.

In accordance with another aspect of the invention, there is provided proofing apparatus for verification of adequacy of compaction or extent of compaction of soil, that includes a first transducer for disposition at the bottom of a defined region, a second transducer for disposition on top of compacted soil in the defined region for verification of adequacy of compaction or extent of compaction of that soil, pulse generating structure for generating a seismic pulse for transmission through the soil material between the first and second transducers, and verifying circuitry responsive to the outputs of the first and second transducers for providing a time (dependent on propagation velocity) indication of energy propagation between the first and second transducers through the soil material to provide an indication of compaction quality.

In a particular proofing apparatus, a chamber of low sonic propagation material such as molded plastic or wood is provided, a first transducer is housed in an isolation cavity in the base of the chamber, a second transducer assembly that includes a sensor and a triggering terminal is provided for disposition on the top of compacted soil material in the chamber and a calibrated sonic impulse generator in the form of a hammer and guide rod is provided for generating a seismic pulse for transmission between the two transducers through the soil material to provide an indication of the quality of the compaction of the soil material in the chamber which may be correlated with a standard test such as the Proctor Test of the California Bearing Ratio test.

In accordance with another aspect of the invention, there is provided a method for proofing the compaction of soil in an excavation region that includes the steps of providing chamber structure of low sonic propagation material, placing sensor structure at the bottom of the chamber structure, placing a sample of soil in the chamber structure and compacting the soil sample to satisfy the criteria of a standard test, measuring the propagation time of an energy wave from the top of soil material in the chamber structure to provide a reference propagation time value indicative of satisfactory compaction, placing transducer structure at the bottom of an excavation region, adding soil material to the excavation region, compacting the soil material in the excavation region with a series of compacting impacts, and measuring the propagation time of an energy wave from the top of the compacted soil material in the excavation region to the transducer structure at the bottom of the excavation region to provide a propagation time value for comparison with the reference propagation time value to obtain an indication of satisfactory compaction of soil in the excavation region.

In accordance with another aspect of the invention, there is provided a method for monitoring the compaction of soil in a defined region or such as a chamber that includes the steps of placing sensor structure at the bottom of the region or chamber, adding soil material or the sensor structure in the to the excavation, compacting the soil material with a series of compacting impacts, and monitoring the output of the sensor structure as a function of seismic energy from the impacts that impinge on the sensor structure.

Preferably, the method includes the steps of accumulating amplitude signals from the sensor structure and comparing the magnitudes of those amplitudes from successive compacting passes; and after backfill has been completed, verifying the quality of soil compaction by measuring the propagation time of an energy wave from the top of the soil material to a sensor at the bottom of the soil material to provide an indication of the quality of the compaction of the soil material.

The invention provides effective real-time monitoring and verification in the field of compaction processes of soil material in a utility excavation or the like.

BACKGROUND OF THE INVENTION

Other features and advantages of the invention will be seen as the following description of particular embodiments progresses, in conjunction with the drawings, in which.

DESCRIPTION OF PARTICULAR EMBODIMENTS

Figure 1:
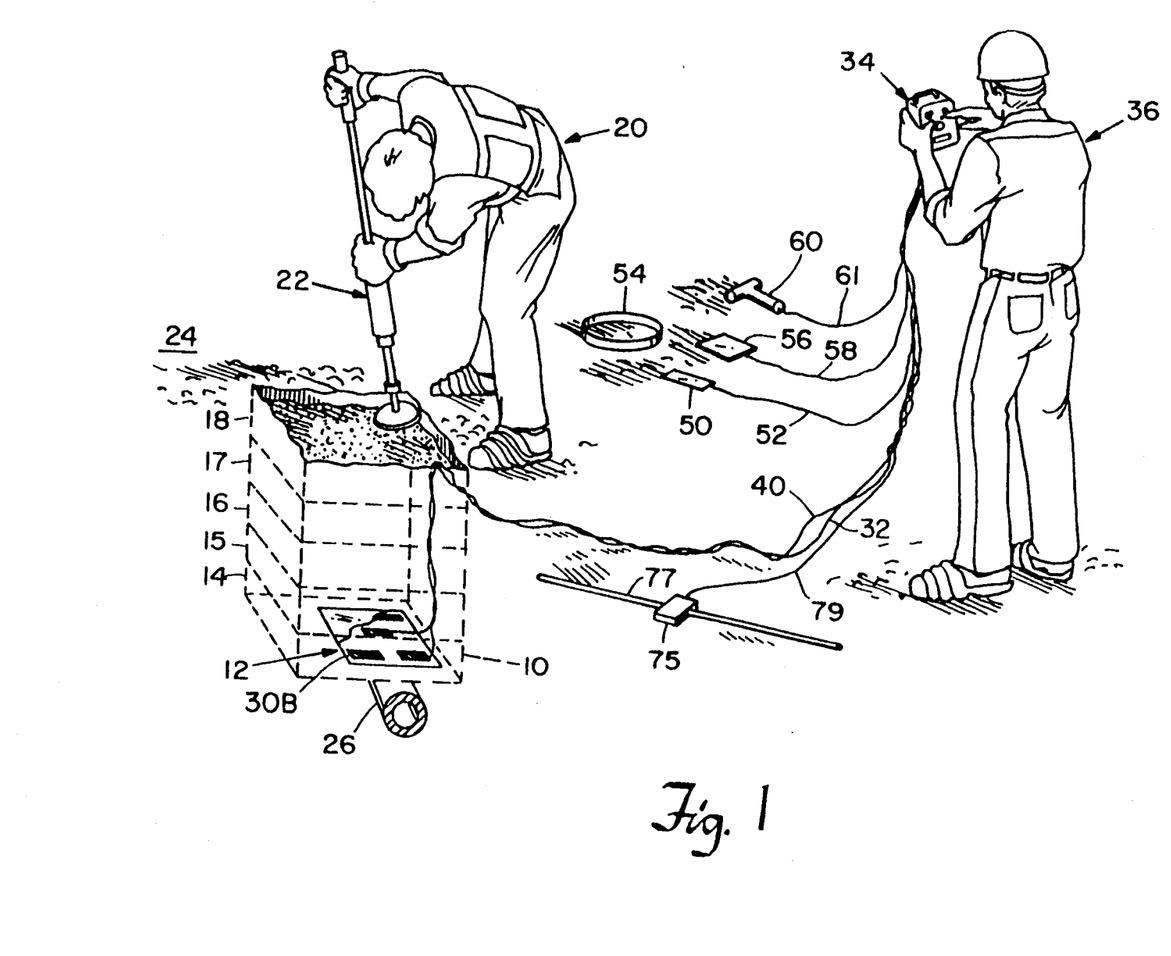
FIG. 1 is a diagrammatic view showing of aspects of a compaction monitoring system in accordance with the invention.

The system diagrammatically shown in FIG. 1 includes excavation 10 in road surface 24 for repair of gas line 26. Gas line 26 has been repaired, sensor module 12 is at the base of excavation 10 and a series of five lifts 14–18 of backfill material are in excavation 10. Operator 20 is using impact tool 22 for compacting the uppermost lift 18. Sensor module 12 has an array of four piezoelectric transducer strips 30A, B, C, D that are connected in parallel by conductors 32 to battery-powered portable control module 34 that is operated by observer 36 and a further piezoelectric transducer strip 38 that is connected by conductors 40 to control module 34.

Figure 2:
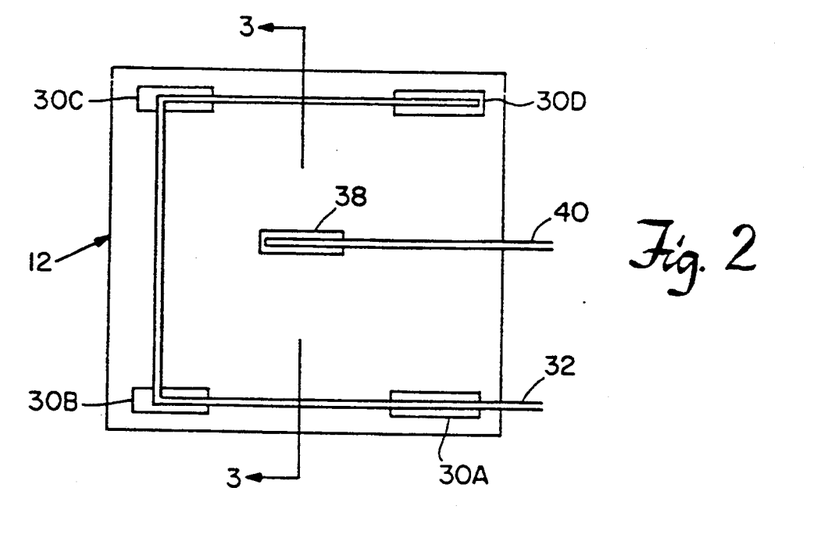
FIG. 2 is a plan view of the sensor module employed in the system of FIG. 1.
Figure 3:
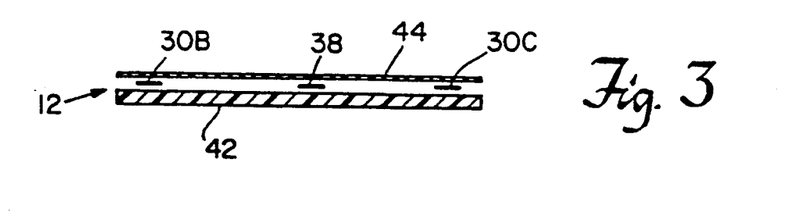
FIG. 3 is a sectional view taken along the line 3—3 of FIG. 2.

Further details of sensor module 12 may be seen with reference to FIGS. 2 and 3. That module includes compliant rubber pad 42 that is about sixty centimeters on a side and has a thickness of about $\frac{1}{2}$ centimeter such that it conforms to the bottom of the excavation 10 and presents the piezoelectric sensors 30, 38 in fixed array. Sensors 30, 38 are of suitable piezoelectric material such as polyvinylidene fluoride (PVDF) film and each film is about two centimeters wide and fifteen centimeters long and metalized for connection to conductors 32, 40. A protective sheet 44 of mylar or similar material overlies and provides protection for sensors 30, 38 and conductors 32, 40 in the excavation 10.

With reference again to FIG. 1, the system also includes PVDF proofing sensor 50 for placement on the surface of the completely backfilled excavation and that is connected to control module 34 by conductor 52, cylindrical spacer 54 (about twenty-five centimeters in diameter and five centimeters high) that is adapted to be placed over sensor 50 and filled with backfill material, metal trigger plate 56 that is placed on the surface of the backfill material in spacer 54 and that is connected to control module 34 by conductor 58, and proofing hammer 60 that is connected to control module 34 by conductor 61. The striking of plate 56 by hammer 60 completes a circuit between conductors 58, 61 to activate circuits in microprocessor 84 in anticipation of a timing cycle for proofing the backfilled excavation. The system also includes a sonic transmitter-receiver unit 75 that is supported on rod 77 and connected to control module by conductor 79, rod 77 being adapted to be positioned on road surface 24 to bridge hole 10 so that unit 75 is positioned directly above sensor 38 of sensor module 12 for sonic depth measurement before any lift of backfill material is placed in excavation 10.

Figure 4:
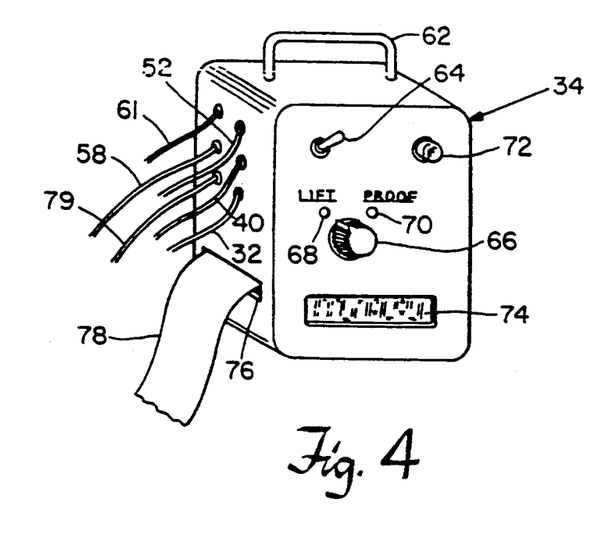
FIG. 4 is a perspective view of the control module employed in the system of FIG. 1.
Figure 5:
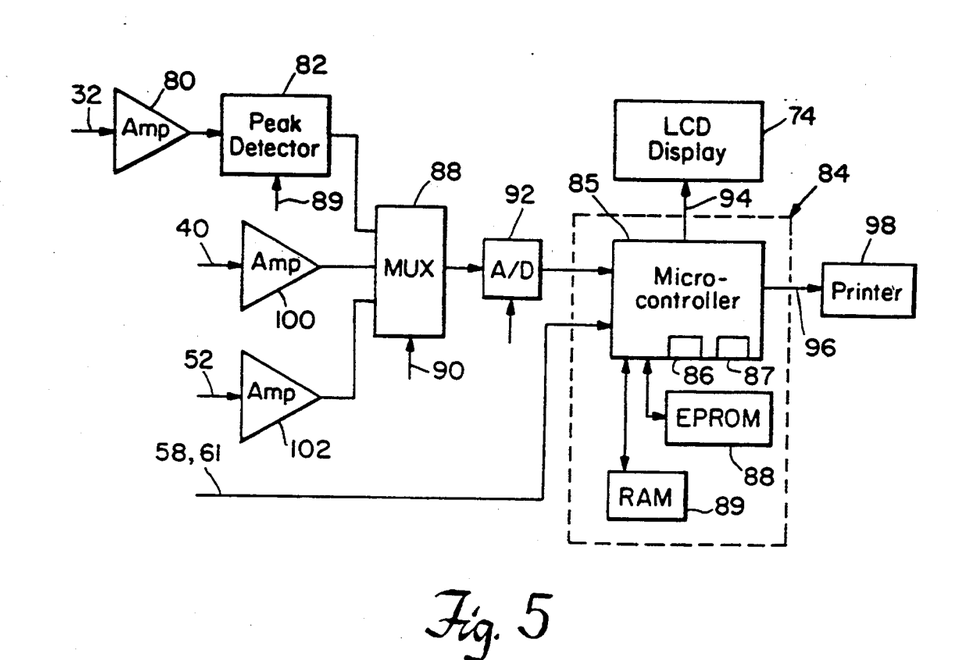
FIG. 5 is a block diagram of circuitry of the control module of FIG. 4.

The portable, battery-powered control module 34 is shown in FIG. 4, and a block diagram of its circuitry is shown in FIG. 5. That module includes carrying handle 62, on/off switch 64, mode selector switch 66 that has compaction mode position 68 and proof mode position 70; reset button 72; LCD display 74 and printer output 76 that produces a printed record 78 of compaction results.

With reference to FIG. 5, input lines 32 (from perimeter sensors 30A–D that are connected in parallel) are connected through adjustable gain amplifier 80 to peak detector 82 that has an input 83 from microprocessor 84. Microcontroller 85 includes accumulator 86 and timing counter 87; and coupled to microcontroller 85 are EPROM 88 and RAM 89. The output of peak detector 82 is applied through multiplex unit 88 that has an input 90 from mode selector switch 66 and analog to digital converter 92 to microcontroller 86 which provides an output over line 94 to LCD display 74 and over line 96 to printer 98. A second input to control module 34 is over lines 40 (from center sensor 38 through adjustable gain amplifier 100 to multiplexer 88); a third input over lines 52 from sensor 50 that is used with proofing hammer 60 and is applied through adjustable gain amplifier 102; and a fourth (trigger) input over line 58 from proofing plate 56 and line 61 from hammer 60. Peak detector 82 includes circuitry that accumulates peak values of signals on line 32 and averages those peak values for application through multiplexer 90 and analog to digital converter 92 for storage by accumulator 86 and display of the average value by display 74. Peak detector 82 is reset periodically (automatically by microcontroller 85) to provide a series of average impact values as sensed by sensors 30A-D. Processor 84 stores the magnitude of those averaged impact values (which increase as the backfill material is compacted and thus better transmits the impact energy to sensors 30) and compares the sensed impact values of preceding passes with those of the current pass and when they are substantially uniform (e.g., the average value of impact generated signals during the current pass being less than five percent greater than the average signal value during the immediately preceding pass), microprocessor 84 causes display 74 to provide an indication of satisfactory compaction of that lift.

Figure 6:
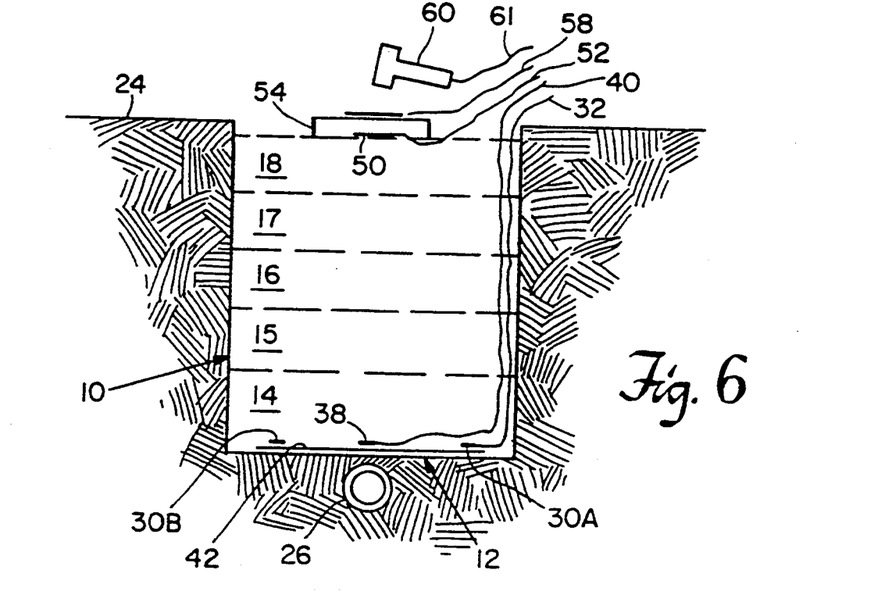
FIG. 6 is a sectional diagrammatic view of system operation in proofing mode.

In system use, with reference to FIG. 6, after gas line 26 at the base of utility excavation 10 has been covered with a thin layer of backfill material, sensor module 12 is placed at the bottom of excavation 10 with connecting conductors 32, 38 leading up out of the excavation to the control module 34. The distance from the central sensor 38 to the top of the hole 10 is measured and entered into control module 34, (for example, manually or with a sonic transmitter-receiver unit 75 that is supported directly above sensor 38 by rod 77 that is positioned on road surface 24 to bridge hole 10 and a depth measurement is made sonically and entered into processor 84). A lift 14 of backfill material is placed in the excavation and compacted with compaction tool 22 which may be manual, pneumatic or hydraulic as appropriate depending on the particular application. As the lift 14 is being compacted in a series of "passes", the compaction is monitored by control module 34 in compaction mode by sensing the amplitude of signals over lines 32 from the perimeter sensors 30. Each compacting blow from compacting tool 22 transmits seismic energy through the backfill lift 14 to the sensors 30 which produce output voltages Proportional to the sensed impact energies. A hydraulic compacting tool typically generates several compacting blows a second, and during each pass, the peak amplitude of signals on lines 32 as indicated by peak detector 82 is read by control module 34 at one hundred millisecond intervals and transferred through multiplexer 90 and A-D converter 92 for storage in accumulator 86. Peak detector 82 is reset automatically by microcontroller 85 after each interval so that a series of average impact values are stored by accumulator 86. Those averaged impact values (which increase as the backfill material is compacted with corresponding improvements of the transmission of impact energy to sensors 30) of a preceding pass are compared with those of the current pass and when the average value of impact generated signals during the current pass is less than a predetermined amount (e.g., five percent) greater than the average impact signal values during the immediately preceding pass, microprocessor 84 causes display 74 to provide an indication of satisfactory compaction of lift 14. Lifts 15-18 are similarly backfilled and compacted.

After the several lifts 14-18 have been satisfactorily compacted in sequence, the distance between the top of the hole 10 (original surface 24) and the surface of lift 18 is measured and entered into control module 34 as an offset from the earlier entered excavation depth measurement. Proofing sensor 50 is placed on the center of the top of lift 18 of the backfill material (immediately above the center sensor 38), spacer 54 is placed on the surface of backfill lift 18 surrounding sensor 50 and is filled with backfill material 79 that is compacted as appropriate to provide a thickness of about five centimeters, and proofing plate 56 is placed on top of the backfilled spacer 54, as indicated in FIG. 6. Mode selector switch 66 is placed in proof mode position 70 and proofing plate 56 is then struck with hammer 60, generating an initializing signal over lines 58, 61 to microprocessor 84 to initialize the microprocessor circuitry that includes timer counter 87. Proofing sensor 50 in response to sonic energy from proofing plate 56 transmits an impulse over lines 52 and through multiplexer 90 to microprocessor 84 to start the timer counter 87. The sonic energy from the hammer 60 striking plate 56 is subsequently sensed by sensor 38 and supplied over lines 40 through amplifier 100 to microprocessor 84 to stop counter 87. The counter value (which represents propagation time between sensors 50 and 38) is then used to calculate velocity, on the basis of the known distance between sensors 38 and 50, as an indication of the quality of compacted backfill in excavation 10. The parameters of that compacted backfill quality can be inputed to microprocessor 84 in terms of characteristics of the backfill material and depth of the excavation (distance between sensors 38 and 50) or the time difference (propagation time) may be displayed directly as an indication of compaction quality in terms of characteristics of the backfill material and depth of the excavation 10 based on empirical data.

Figure 7:
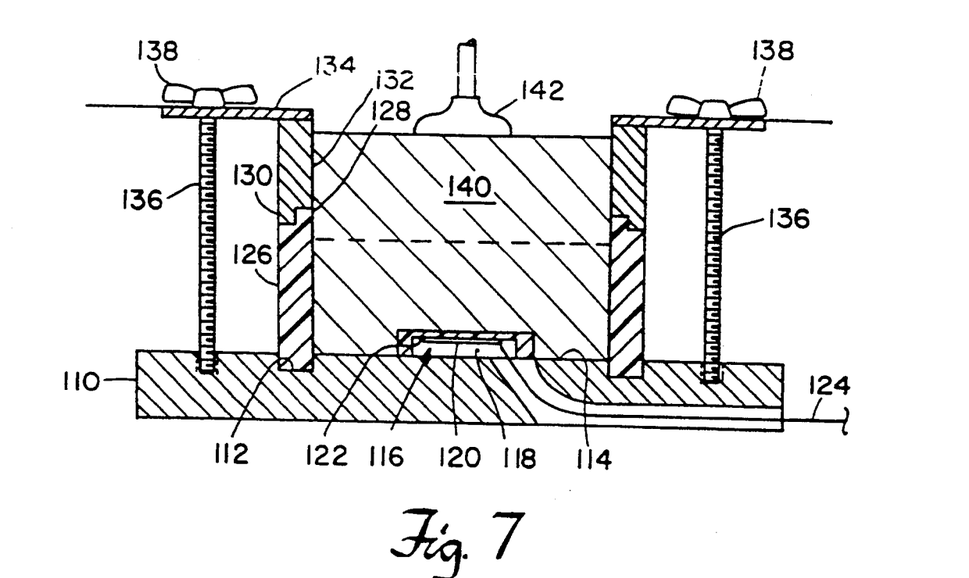
FIG. 7 is a sectional diagrammatic view of a second system in accordance with the invention.
Figure 8:
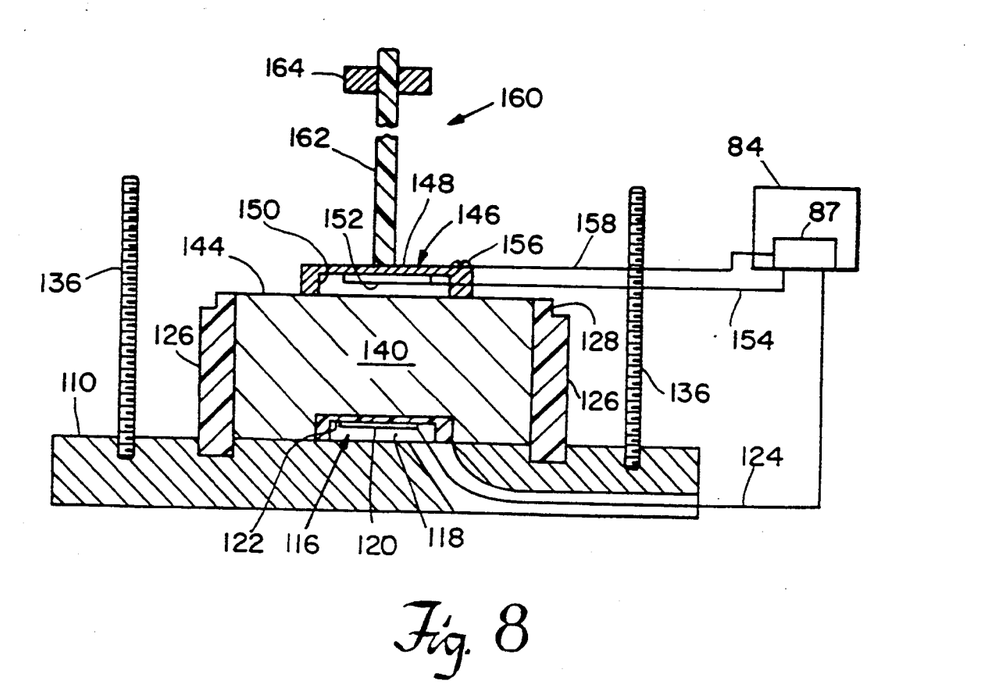
FIG. 8 is a sectional diagrammatic view of a second stage of operation of the system shown in FIG. 7.

With reference to FIG. 7, a field proofing test (FPT) device thereshown includes wood base 110 that has a thickness of about six centimeters and is of square configuration about 0.7 meters on a side. Groove 112 has a width of about two centimeters, a depth of about two centimeters and an inner diameter of about thirty-two centimeters. Seated on surface 114 is polyvinylchloride housing 116 that defines isolation chamber 118 with PVDF film sensor 120 secured on the inner surface of upper wall 122 and connected by lead 124 to monitoring circuitry of the type shown in FIG. 5. Housing 116 has a width of about seven centimeters, a length of about fourteen centimeters and a height of about four centimeters, and upper wall 122 has a thickness of about one centimeter.

Seated in groove 112 is polyvinylchloride cylinder 126 that has an inner diameter of about thirty-two centimeters, a height of about twenty-three centimeters and a wall thickness of about two centimeters, with annular lip 128 at its top wall surface. Seated on and mating with lip 128 is lip 130 of aluminum cylinder 132 as an extension of cylinder 126 with a height of about fifteen centimeters. Aluminum plate 134 is welded to and extends horizontally from the top of cylinder 132 and has holes as its four corners that receive corresponding threaded tie-rods 136 that are secured to and upstanding from base 110. Wing nuts 138 that are received on tie-rods 136 securely seat aluminum cylinder 132 on PVC cylinder 126.

Figure 9:
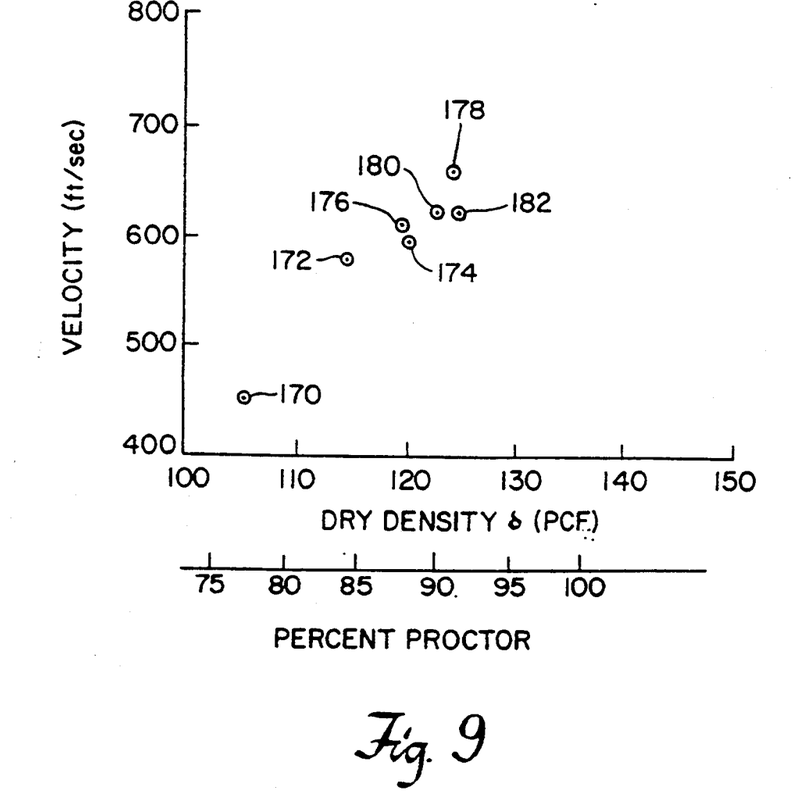
FIG. 9 is a graph indicating correlation between Proctor Test laboratory measurements and field use of the system shown in FIGS. 7 and 8.

In use of the field proofing test (FPT) device, cylinders 126, 132 are filled in two lifts with a soil 140 to be tested, each lift being compacted with a tamper that has a fifteen centimeter diameter foot 142 to uniformly compact the soil in base cylinder 126. After compaction, wing nuts 138 are released, the upper cylinder 132 is removed with care to avoid excessive disturbance of the soil 140 and the compacted soil 140 is carefully levelled as indicated in FIG. 9 so that the top surface 144 of soil 140 is level with the top of cylinder 126.

Proofing sensor assembly 146 includes aluminum strike plate 148 that is about six centimeters square and about two centimeters thick with 0.6 centimeter deep recess 150 in which is secured PVDF film sensor 152 that is connected by lead 154 to monitoring apparatus 84. Attached to plate 148 by screw 156 is lead 158. Calibrated hammer assembly 160 includes polyvinylchloride guide rod 162 that has a length of about fifty centimeters and receives steel hammer member 164 of about five centimeters outer diameter and that weighs about 0.5 kilogram.

When proofing hammer 164 is dropped from a height of forty centimeters on striking plate 148 a signal is produced over line 158 to microprocessor 84B to initialize the microprocessor circuitry 84 that includes timer counter 87 in anticipation of a timing cycle for measuring the quality of compaction of the soil 140. Proofing sensor 152 in response to sonic energy from plate 144 transmits an impulse over line 158 to the microprocessor 84 to start the timing counter 87. The seismic energy transmitted through soil 140 is sensed by sensor 120 and transmitted over line 124 as a second input to counter 87 and the resulting counter value (which represents propagation time between sensors 152 and 120) is used to calculate propagation velocity which correlates with Proctor Test data obtained in the laboratory. An indication of this correlation in a gravelly sand that has a Proctor of 146.2 PCF at 6.7 percent moisture is shown in FIG. 9, the soil 140 without compaction (point 170 has a percent Proctor of about 78 at a velocity of about 450 feet per second; compaction of two seconds time (point 172) results in a seismic velocity of 580 feet per second (about 85 percent Proctor); compaction of about five seconds (points 174 and 176) results in a seismic velocity of about 600 feet per second which corresponds to a percent Proctor of about 87 percent; ten seconds compaction (points 178 and 180) produces seismic velocities of about 660 feet per second which corresponds to about 92 percent Proctor; and tamping for about twenty seconds (point 182) also produces similar sonic velocities and percent Proctor in this soil.

Using that data as an example, if it is desired to have a minimum of 90 percent Proctor in the excavation, then the operator loads the FPT with the unknown soil, and compacts for a minimum of ten seconds to achieve a minimum of 90 percent Proctor. A velocity measurement using the procedure described above finds that soil exhibits a velocity of 625 feet per second. The 625 feet per second value becomes the performance goal for compaction of the backfill material in the field.

While particular embodiments of the invention have been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. Proofing apparatus for verification of adequacy or extent of compaction of soil comprising
    a first transducer for disposition at the bottom of a defined region,
    a second transducer for disposition on top of compacted soil in the defined region for verification of adequacy of compaction or extent of compaction of that soil,
    pulse generating structure for generating a seismic pulse for transmission through the soil material between said first and second transducers, and
    verifying circuitry responsive to the outputs of said first and second transducers for providing a time (dependent on propagation velocity) indication of energy propagation between said first and second transducers through the soil material to provide an indication of compaction quality.

2. A method for proofing the compaction of soil in an excavation region comprising steps of
    providing chamber structure of low sonic propagation material,
    placing first sensor structure at the bottom of said chamber structure,
    placing a sample of soil in said chamber structure and compacting said soil sample to satisfy a criterion of a standard test,
    measuring the propagation time of an energy wave from the top of soil material in said chamber structure to provide a reference propagation time value indicative of satisfactory compaction,
    placing transducer structure at the bottom of an excavation region,
    adding soil material to said excavation region,
    compacting said soil material in said excavation region with a series of compacting impacts, and
    measuring the propagation time of an energy wave from the top of said compacted soil material in said excavation region to said transducer structure at the bottom of said excavation region to provide a propagation time value for comparison with said reference propagation time value to obtain an indication of satisfactory compaction of soil in said excavation region.

3. The method of claim 2 and further including the step of accumulating a plurality of impact signals from said transducer structure during a compaction pass to provide an indication of the progress of the compaction process.

4. The method of claim 2 wherein said transducer structure includes a compliant base member of electrically-insulating material on which a plurality of piezoelectric transducers are secured in spaced array, and said base member has an area at least about one-half the base area of said excavation.

5. The method of claim 4 and further including a compaction mode step that includes accumulation of a plurality of impact signals from said transducers during a compaction pass to provide an indication of the progress of the compaction process, and a proofing mode step that includes measuring the propagation time of an energy wave from the top of soil material in said defined region to a piezoelectric transducer at the bottom of said defined region to provide an indication of the quality of the compaction of the soil material in said defined region.

6. Proofing apparatus for verification of adequacy or extent of compaction of soil comprising
- a first transducer for disposition at the bottom of a defined region, chamber structure of low sonic propagation material, isolation cavity structure in a base of said chamber structure for housing said first transducer
- a second transducer for disposition on top of compacted soil in the defined region for verification of adequacy of compaction or extent of compaction of that soil,
- said second transducer assembly including sensor and triggering terminal structure for disposition on top of compacted soil material in said chamber,
- pulse generating structure for generating a seismic pulse for transmission through the soil material between said first and second transducers, said pulse generating structure including hammer and guide structure for generating a seismic pulse for transmission between said two transducers through the soil material to provide an indication of the quality of the compaction of the soil material in the chamber which may be correlated with a standard test, and
- verifying circuitry responsive to the outputs of said first and second transducers for providing a time dependent on propagation velocity) indication of energy propagation between said first and second transducers through the soil material to provide an indication of compaction quality.

* * * * *